(12) United States Patent
Kormann

(10) Patent No.: US 8,347,709 B2
(45) Date of Patent: Jan. 8, 2013

(54) MEASUREMENT APPARATUS FOR MASS FLOW DETECTION OF HARVESTED CROPS

(75) Inventor: Georg Kormann, Zweibrücken (DE)

(73) Assignee: Deere & Company, Moline, IL (US)

(*) Notice: Subject to any disclaimer, the term of this patent is extended or adjusted under 35 U.S.C. 154(b) by 300 days.

(21) Appl. No.: 12/936,851

(22) PCT Filed: Apr. 7, 2009

(86) PCT No.: PCT/EP2009/054111
§ 371 (c)(1),
(2), (4) Date: Oct. 7, 2010

(87) PCT Pub. No.: WO2009/124919
PCT Pub. Date: Oct. 15, 2009

(65) Prior Publication Data
US 2011/0030469 A1 Feb. 10, 2011

(30) Foreign Application Priority Data
Apr. 8, 2008 (DE) .................. 10 2008 017 670

(51) Int. Cl.
*G01F 3/12* (2006.01)
(52) U.S. Cl. .................... 73/272 R; 73/861.73

(58) Field of Classification Search .......... 73/272 R, 73/861.73, 149, 861, 218
See application file for complete search history.

(56) References Cited

U.S. PATENT DOCUMENTS

| 1,875,725 A * | 9/1932 | Hartley ............ 73/218 |
| 3,278,747 A * | 10/1966 | Ohmart ............ 378/54 |
| 5,750,877 A * | 5/1998 | Behnke et al. ........ 73/1.33 |
| 6,282,967 B1 * | 9/2001 | Homburg et al. ...... 73/861 |
| 2002/0014116 A1 | 2/2002 | Campbell et al. |

FOREIGN PATENT DOCUMENTS

| DE | 4200770 | 7/1993 |
| DE | 19541167 | 5/1997 |
| DE | 19544057 | 5/1997 |
| DE | 19802756 | 7/1999 |
| DE | 19808148 | 9/1999 |
| SU | 1451554 | 1/1989 |

* cited by examiner

Primary Examiner — Jewel V Thompson

(57) ABSTRACT

The invention relates to a measurement apparatus for detecting the mass flow of harvested crops which are conveyed by means of a conveyor. The measurement apparatus comprises a first measuring device for weighing the conveyor together with the conveyed harvested crops, a second measuring device for determining the volume of the harvested crops conveyed by the conveyor, and a computer device for determining the mass density of the harvested crops.

19 Claims, 3 Drawing Sheets

MEASUREMENT APPARATUS FOR MASS FLOW DETECTION OF HARVESTED CROPS

This application claims priority from International Application No. EP2009054111, filed on Apr. 7, 2009, and incorporated herein by reference.

FIELD OF THE INVENTION

The invention relates to a method and a measurement apparatus for detecting the mass flow of harvested crops which are conveyed by means of a conveyor.

BACKGROUND ART

In the harvesting of agricultural products, such as, for example, grain, there is a need to detect the respective throughput of harvested crops, whether this be geo-referenced for use in precision agriculture or cumulative for the purpose of exact accounting in paid harvesting work.

Measuring devices have been proposed which detect the volume of the harvested material optically (e.g., DE 198 02 756 A). What is to be considered as a disadvantage here is that the volume can indeed be detected, but not the mass or gravitational force of the material, which is substantially more relevant for said purposes than the volume. A detection of the density of the material and a conversion of the volume into a mass are conceivable, but are complicated and are susceptible to faults on account of the frequently and briefly changing densities of the harvested material.

Furthermore, it has been proposed to detect the mass of the harvested material by weighing the entire grain elevator of a combine harvester (e.g., DE 195 44 057 A). This measurement presents problems in the case of smaller throughputs of harvested crops, since the mass of the harvested crops is then substantially lower than the weighed mass of the grain elevator. A poor signal-to-noise ratio is consequently obtained, which is further impaired by vibrations of the harvesting machine and shocks when the harvesting machine travels over uneven ground.

DE 195 41 167 A describes a combine harvester in which the volume of the harvested crops in the grain elevator is detected optically. Furthermore, downstream of the grain elevator, a calibrating device is provided, in the form of a container which is equipped with a balance and into which, when quantity measurement is switched on, the harvested crops are diverted at specific time rates upon an operator's input or after a change in the type of harvested crops. The calibrating device serves for detecting the mass of a quantity of the harvested crops, the volume of which is likewise known, so that the optically detected volume of the harvested crops can subsequently be converted into a mass on the basis of the values of the calibrating device. There is still the disadvantage here, likewise, that the density of the harvested crops may change briefly, but, in unfavorable cases, this cannot be detected or can be detected only late by the calibrating device which becomes active only from time to time, so that there is still the risk of faulty measurement values for the mass.

DE 42 00 770 A describes a measurement apparatus for determining the fillability of tobacco material which is correlated with the density. The material is transported on a conveyor belt and the height of the material above the conveyor belt is detected by means of a laser sensing device, while the volume of the material is determined on the basis of the known conveying speed. At the same time, the conveyor belt is weighed, in order to determine the mass of the material. The density is then calculated by dividing the mass by the volume in order to obtain information on the fillability of the material. Since the throughput is essentially constant because the measurement apparatus is used in the cigarette production plant, the mass values which are susceptible to faults in the case of lower throughputs and which may arise due to the weighing of the conveyor belt together with the material do not present any problems with regard to the application described. On account of these faults, however, the measurement apparatus is not suitable for use in harvesting machines.

Finally, DE 198 08 148 A, considered as generic, describes an arrangement for determining the earth mass fraction in conveyed streams of agricultural products, such as sugar beet or potatoes. The harvested crops are transported on a chain conveyor. The volume of the harvested crops is detected by means of a laser scanner sensing their surface, while the mass of the harvested crops is determined by weighing the chain conveyor. The density of the harvested crops is calculated by dividing the mass by the volume, and, finally, the earth fraction in the harvested crop is determined on the basis of a stipulated known standard bulk density. Even here, the problem that mass determination is susceptible to faults in the case of lower throughputs is not solved.

SUMMARY

A measurement apparatus is associated with a conveyor on which harvested crops are conveyed through a harvesting machine. The measurement apparatus comprises a first measuring device that measures the weight of the conveyor and harvested crops, a second measuring device that measures the volume of the crops, and a computer device that calculates the mass density and mass flow based on the weight measured by the first measuring device and the volume measured by the second measuring device.

DETAILED DESCRIPTION OF THE PREFERRED EMBODIMENT(S)

Figure 1:
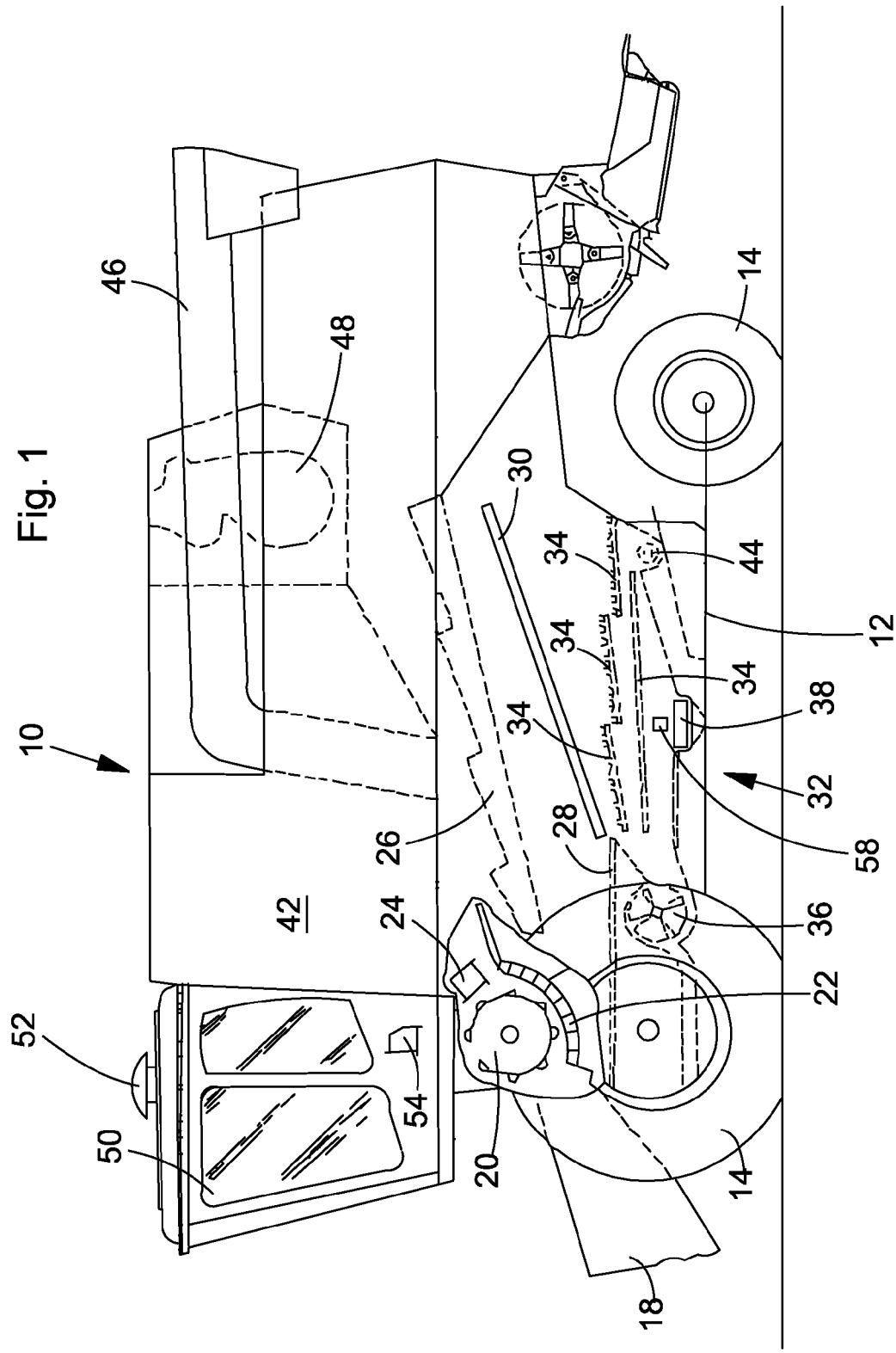
FIG. 1 shows a diagrammatic side view of a combine harvester with a conveyor for conveying away the cleaned grain, which conveyor is assigned a measurement apparatus according to the invention.

A measurement apparatus for detecting the mass flow of harvested crops conveyed by means of a conveyor comprises a first measuring device, by means of which the conveyor, together with the harvested crops conveyed by it, is weighed. A second measuring device is provided for determining the volume of the harvested crops conveyed by the conveyor. A computer device continuously calculates the mass density of the harvested crops by means of the measurement values of the first measuring device and of the second measuring device and stores them. In the case of throughputs lying above a threshold value, the computer device determines mass flows and uses them as an output value, these mass flows being based only on the current measurement values of the first measuring device. This threshold value may lie at a specific percentage of the maximum expected mass flow or volume throughput, for example at 10%. If the throughputs lie below the threshold value, the computer device determines mass flows and outputs them, these mass flows being based on the current measurement values of the second measuring device and on the value for the mass density of the harvested crops which, in the case of the last throughput lying above the threshold value, was determined on the basis of the measurement values of the first measuring device and of the second measuring device.

Thus, the accuracy of the measurement apparatus is increased, since, in the case of lower throughputs at which the measurement values of the first measuring device detecting the gravitational force or mass of the conveyor are not sufficiently accurate, the substantially more accurate measurement values of the second measuring device are adopted. The latter are converted into mass flows by means of the last reliably detectable mass density of the harvested crops.

The second measuring device preferably comprises a contactless range finder, in particular a laser range finder, which is suitable for the optical sensing of the surface of the conveyor or of the harvested crops located on it and which senses the surface of the conveyor transversely to the conveying direction and/or in the conveying direction.

A conveyor which may be considered is, for example, a belt conveyor. However, the invention may also be used on other types of conveyors, for example on paddle elevators, the conveying volume of which can be detected optically, as described in DE 198 02 756 A, and the gravitational force of which can be detected by weighing the entire paddle elevator at its suspension.

In a transitional range lying, for example, between 10% and 50% of the maximum expected throughput, the computer device can carry out a plausibility check between the measurement results of the first measuring device and of the second measuring device and, in the case of implausibilities, can give a warning to the operator or can ignore the values of the measuring device having the values which appear to be implausible and calculate the mass flow on the basis of the measurement values of the other measuring device in each case.

The measuring device according to the invention is preferably used on harvesting machines, such as combine harvesters.

FIG. 1 shows a self-propelled combine harvester 10 with a carrying frame 12 which is supported on the ground via front driven and rear steerable wheels 14 and which is moved forward by these. The wheels 14 are set in rotation by a drive means, not shown, in order to move the combine harvester 10, for example, over a field to be harvested. A harvested crop recovery device (not shown) in the form of a cutting mechanism or maize picker or the like can be connected to the front end region of the combine harvester 10, in order to harvest crops from the field and deliver them upwardly and rearwardly by means of a slope conveyor 18 to a threshing device having a transversely arranged threshing drum 20 and a threshing basket 22 assigned to the latter. The harvested crops are then delivered via a turning drum 24 to a straw rocker 26. All the direction indications, such as front, rear, above and below, refer below to the forward travel direction of the combine harvester 10.

Grains and chaff which are separated during the threshing operation fall onto a preparation floor 28. Grains and chaff which, however, are separated by the straw rocker 26 fall onto a vibrating floor 30 which guides them onto the preparation floor 28. The preparation floor 28 transfers the grains and chaff to a cleaning device 32 with screens 34 arranged in it, which is assigned a blower 36 in order to assist the separation of the chaff from the grains. Cleaned grains are delivered by means of a conveyor 38 to an elevator 40 (see FIG. 3) which conveys them into a grain tank 42. A turnover worm 44 returns ear fragments not threshed out to the threshing process by means of a further elevator, not shown, that is to say delivers them to the threshing drum 20 again. The chaff is discharged on the rear side of the cleaning device 34. The cleaned grains from the grain tank 42 can be unloaded by means of an unloading system with transverse worms and with an unloading conveyor 46.

Said systems are driven by means of an internal combustion engine 48 and are controlled by an operator from a driver's cab 50. The various devices for threshing, conveyance, cleaning and separation are located inside the carrying frame 12.

For geo-referenced yield detection, the combine harvester 10 is assigned an antenna 52 for the reception of signals from a satellite-assisted position detection system (for example, GPS) and a computer device 54 connected to the antenna 52. Furthermore, the computer device 54 is connected (wirelessly, for example by radio, or optically or wire-bound, for example via a bus line) to two measuring devices 56, 58 which cooperate with the conveyor 38. The computer device 54 forms with the measuring devices 56, 58 a measurement apparatus for detecting the mass flow of the harvested crops conveyed by the conveyor 38 and records the mass flow with geo-referencing.

Figure 3:
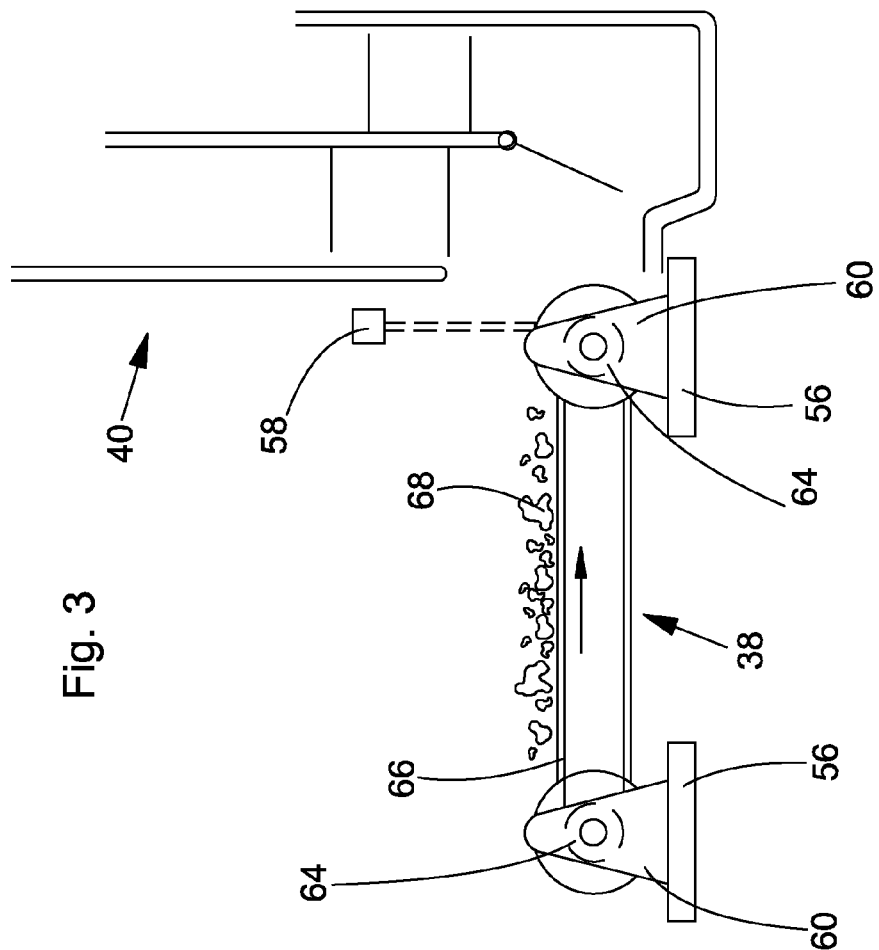
FIG. 3 shows a view of the conveyor from the front.
Figure 2:
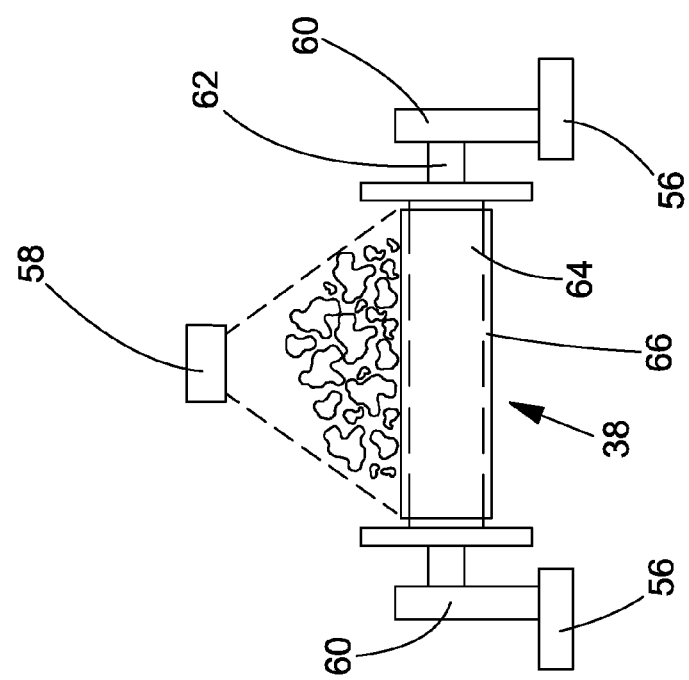
FIG. 2 shows a side view of the conveyor with two measuring devices.

It can be seen from FIGS. 2 and 3 that the first measuring device 56 comprises, overall, four force sensors in the form of strain gauges or other suitable sensors for detecting the gravitational force of the conveyor 38. The four force sensors are in each case arranged between the carrying frame 12 and one of four mountings 60, on which a driven shaft and a freely co-rotating axle 62 are supported, which hold rollers 64, around which runs a conveyor belt 66, on the top side of which the cleaned harvested crops transferred from the cleaning device 32 are conveyed to the elevator 40. The first measuring device 56 accordingly detects the gravitational force of the conveyor 38. Furthermore, it would be conceivable to assign to the first measuring device 56 means for the compensation of shocks which may be caused, for example, by unevennesses of the ground, which means may comprise, for example, accelerometers.

The second measuring device 58 is designed as a laser range finder sensing the surface of the conveyor 38 in the transverse direction. The height of the harvested crops 68 above the conveyor belt 66 is determined by means of the transit time of the light radiated from the second measuring device 58 to conveyor 38 and reflected from the latter to the second measuring device 58 again. In this case, gradually, a plurality of measurement values are detected over the width of the conveyor belt 66. Furthermore, the computer device 54 (or the second measuring device 58) receives from a speed sensor 70 information on the respective conveying speed of the conveyor 38, in order, by a continuous integration of the detected height values of the harvested crops 68 over one revolution of the conveyor belt 66, to determine the volume of the harvested crops 68 which is associated with a detection of the gravitational force by means of the first measuring device 56. Reference may be made, in this respect, to the disclosures of DE 42 00 770 A and DE 198 08 148 A which are also incorporated by reference into the present documents. The speed sensor 70 may be a radar sensor cooperating with the lower strand of the conveyor belt 66 or may detect the rotational speed of the shaft or of the axle 62. The speed of the conveyor 38 may, depending on the type of crop and/or on the maximum expected throughput in each case, be set permanently or be regulated as a function of the current throughput, so that maximum resolution over the measurement range can be achieved, especially when the speed of the conveyor 38 is automatically set in such a way as always to achieve a sufficient covering of the conveyor 38 with harvested crops 68 which allows a sufficiently accurate measurement by means of the first measuring device 36. This also makes it possible that the density value can be detected very quickly at the start of the field in the case of low throughputs, in that the conveyor 38 is then run sufficiently slowly.

Figure 4:
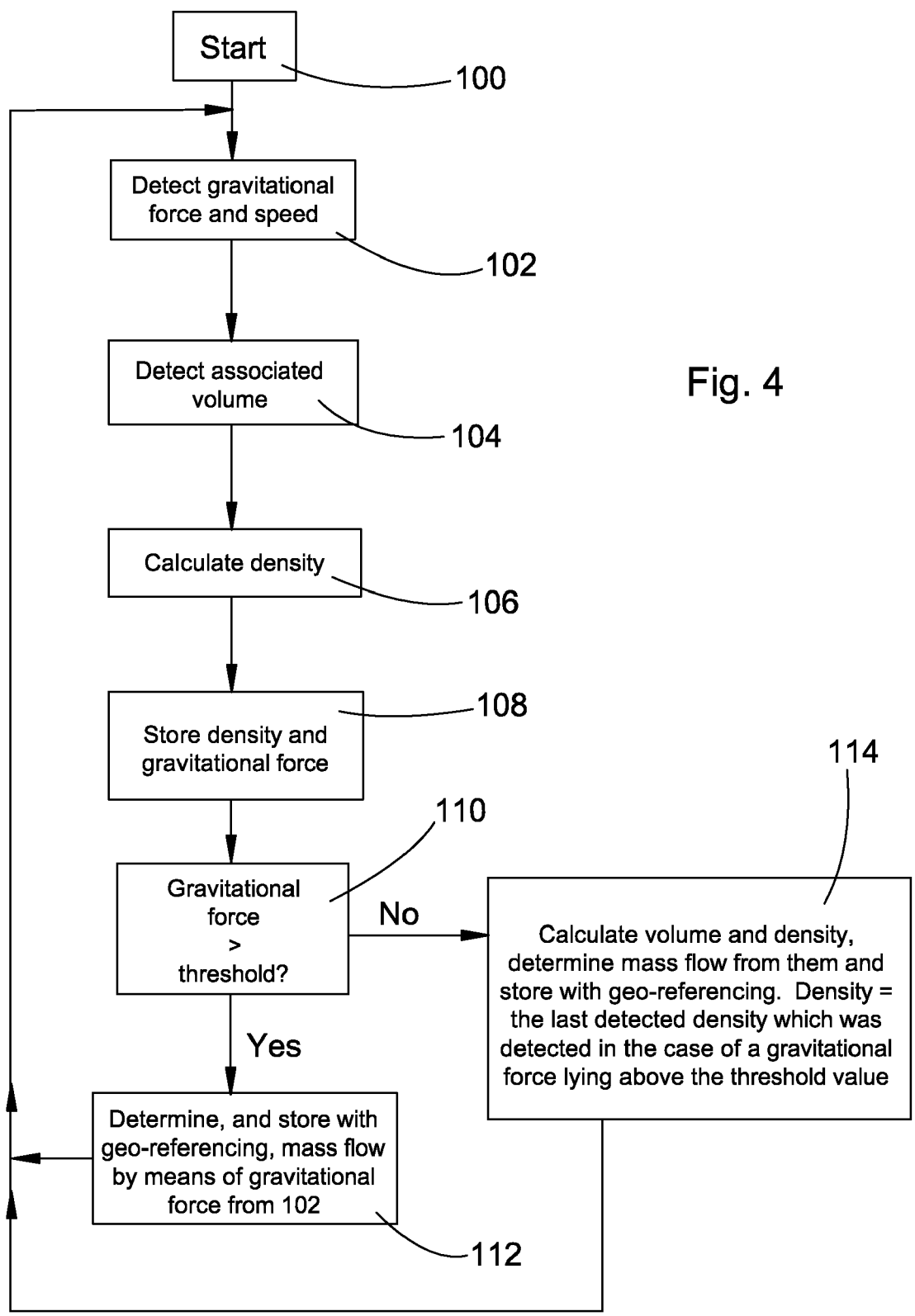
FIG. 4 shows a flowchart according to which the computer device of the measurement apparatus operates.

In harvesting operation, the computer device 54 proceeds according to the flowchart illustrated in FIG. 4. After the start in step 100, in step 102 the gravitational force detected by the first measuring device 56 is interrogated, and the speed of the conveyor belt 66 is interrogated by the speed sensor 70. In the following step 104, the height profile of the harvested crops 68 above the conveyor belt 66 is then recalled by the second measuring device 58 and is converted by means of the signal from the speed sensor 70 into a volume measurement value assignable to the gravitational force measurement value previously obtained by the first measuring device 56, as described above. This is followed by step 106 in which the mass density of the harvested crops is calculated by dividing the mass corresponding to the gravitational force by the volume. The mass density and the associated gravitational force are stored in the following step 108.

The step 110 follows, in which it is interrogated whether the gravitational force is higher than a threshold value which, for example, corresponds to 10% of the maximum expected gravitational force. If this is so, in step 112 which then follows, the gravitational force detected in step 102 and the speed of the conveyor 38 are used in order to determine the mass flow (for this purpose, to be precise, the gravitational force measured in Newtons is divided by the gravitation constant g=9.81 m/s and the result is then multiplied by the speed of the conveyor 38 and divided by the length, measured in the conveying direction, of that part of the conveyor belt 66 which is loaded with harvested crops 68). This mass flow, which can be converted into a yield value measured in kg/m² on the basis of the speed of advance (measured by means of a sensor not shown) of the combine harvester and of the cutting mechanism width, is stored with a geo-referencing. The mass flow determined may also be indicated to the operator and used for the automatic regulation of the speed of advance of the combine harvester and/or for the automatic setting of parameters of the threshing and/or cleaning device. Moreover, the mass density can be stored.

If, by contrast, it is found in step 110 that the gravitational force is lower than or equal to the threshold value, step 114 follows. Since the measurement value of the first measuring device 56 is then insufficiently accurate, the more accurate measurement value of the second measuring device 58 is adopted, which, by means of the last mass density stored in the case of reliable measurement values of the first measuring device, is converted into a mass flow (for this purpose, to be precise, the volume is multiplied by the mass density measured in kg/m³ and multiplied by the speed of the conveyor 38 and is divided by the length, measured in the conveying direction, of that part of the conveyor belt 66 which is loaded by harvested crops 68). In this case, the mass density is used, which, in the case of the last throughput lying above the threshold value, was determined by means of the measurement values of the first measuring device 56 and of the second measuring device 58 and was stored by the computer device 54. The mass thus determined and the speed are used in order to determine the mass flow. This mass flow, which can be converted into a yield value measured in kg/m² on the basis of the speed of advance (measured by means of a sensor not shown) of the combine harvester and of the cutting mechanism width, is stored with geo-referencing. Moreover, the associated mass density can be stored. The determined mass flow can also be indicated to the operator and used for the automatic regulation of the speed of advance of the combine harvester and/or for the automatic setting of parameters of the threshing and/or cleaning device. Step 102 finally follows again.

The following is claimed:

1. A measurement apparatus for determining a mass flow of harvested crops conveyed by a conveyor, comprising:
    a first measuring device for determining a weight of the conveyor and the harvested crops,
    a second measuring device for determining a volume of the harvested crops, and
    a computer device connected to the first measuring device and the second measuring device for calculating a mass density and the mass flow of the harvested crops using the weight and the volume,
    wherein the computer device calculates the mass flow using only the weight currently determined by the first measuring device when a throughput is greater than a threshold and,
    wherein the computer device calculates the mass flow using the volume currently determined by the second measuring device and the mass density of the harvested crops when the throughput is less than the threshold.

2. The measurement apparatus as claimed in claim 1, wherein the second measuring device comprises a range finder for sensing a surface of the conveyor.

3. The measurement apparatus as claimed in claim 2, wherein the range finder senses the surface in a transverse direction or longitudinal direction of the conveyor.

4. The measurement apparatus as claimed in claim 1, wherein information regarding a speed of the conveyor is delivered to the computer device.

5. The measurement apparatus as claimed in claim 1, wherein the conveyor is a belt conveyor.

6. The measurement apparatus as claimed in claim 1, wherein the speed of the conveyor is variable.

7. The measurement apparatus as claimed in claim 6, wherein the speed of the conveyor is set based on the type of crop or on a maximum expected throughput.

8. The measurement apparatus as claimed in claim 6, wherein the speed of the conveyor is regulated as a function of the throughput, such that a sufficient covering of the conveyor with harvested crops is achieved.

9. The measurement apparatus as claimed in claim 1, wherein the computer device compares the weight to an expected weight range and the volume to an expected volume range and, wherein the computer device calculates the mass flow using only the volume when the weight is outside the expected weight range, and wherein the computer device calculates the mass flow using only the weight when the volume is outside the expected volume range.

10. A measurement apparatus as claimed in claim 1 wherein the measurement apparatus is installed on a harvesting machine.

11. A method for determining a mass flow of harvested crops conveyed by a conveyor, comprising:
    determining a weight of the conveyor and the harvested crops using a first measuring device,
    determining a volume of the harvested crops using a second measuring device,
    calculating a mass density of the harvested crops using the weight and the volume,
    storing the mass density, calculating the mass flow using only the weight currently determined by the first measuring device when a throughput is greater than a threshold, and calculating the mass flow using only the volume currently determined by the second measuring device when the throughput is less than the threshold.

12. The method as claimed in claim 11 further comprising sensing a surface of the conveyor by means of the second measuring device.

13. The method as claimed in claim 12 wherein the second measuring device senses the surface in a transverse direction or longitudinal direction of the conveyor.

14. The method as claimed in claim 11 further comprising delivering information regarding a speed of the conveyor to the computer device.

15. The method as claimed in claim 14 wherein the speed of the conveyor is set based on the type of crop or on a maximum expected throughput.

16. The method as claimed in claim 14 wherein the speed of the conveyor is regulated as a function of the throughput, such that a sufficient covering of the conveyor with harvested crops is achieved.

17. The method as claimed in claim 11 further comprising:

comparing the weight to an expected weight range and the volume to an expected volume range, calculating the mass flow using only the volume when the weight is outside the expected weight range, and calculating the mass flow using only the weight when the volume is outside the expected volume range.

18. The method as claimed in claim 11 further comprising:

comparing the weight to an expected weight range and the volume to an expected volume range, and providing an audible or visual warning to an operator when the weight is outside the expected weight range or the volume is outside the expected volume range.

19. The measurement apparatus as claimed in claim 1, wherein the computer device compares the weight to an expected weight range and the volume to an expected volume range, and wherein the computer device provides an audible or visual warning to an operator when the weight is outside the expected weight range or the volume is outside the expected volume range.

* * * * *